(12) United States Patent
Andon et al.

(10) Patent No.: US 11,019,931 B2
(45) Date of Patent: *Jun. 1, 2021

(54) SPORT CHAIR WITH GAME INTEGRATION

(71) Applicant: NIKE, Inc., Beaverton, OR (US)

(72) Inventors: Christopher Andon, Portland, OR (US); Ciro Fusco, Portland, OR (US); Daniel A. Judelson, Portland, OR (US); Hien Tommy Pham, Happy Valley, OR (US); Michael Wallans, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,079

(22) Filed: May 22, 2020

(65) Prior Publication Data
US 2020/0281365 A1  Sep. 10, 2020

Related U.S. Application Data

(63) Continuation of application No. 15/950,158, filed on Apr. 10, 2018, now Pat. No. 10,694,857.

(Continued)

(51) Int. Cl.
| | | |
|---|---|---|
| A47C 7/74 | (2006.01) |
| A43B 3/00 | (2006.01) |
| A47C 7/72 | (2006.01) |
| A47C 1/00 | (2006.01) |
| A61B 5/00 | (2006.01) |
| A61B 5/08 | (2006.01) |
| A61B 5/01 | (2006.01) |
| A61B 5/024 | (2006.01) |
| A61B 5/0533 | (2021.01) |
| A47C 7/50 | (2006.01) |
| A47C 3/12 | (2006.01) |

(Continued)

(52) U.S. Cl.
CPC .............. *A47C 7/744* (2013.01); *A43B 3/001* (2013.01); *A43B 3/0005* (2013.01); *A47C 1/00* (2013.01); *A47C 3/12* (2013.01); *A47C 7/503* (2013.01); *A47C 7/72* (2013.01); *A47C 7/723* (2018.08); *A47C 7/727* (2018.08); *A47C 7/748* (2013.01); *A61B 5/01* (2013.01); *A61B 5/024* (2013.01); *A61B 5/0533* (2013.01); *A61B 5/0816* (2013.01); *A61B 5/4836* (2013.01); *A61B 5/4875* (2013.01); *A61B 5/6823* (2013.01); *A61B 5/6828* (2013.01); *A61B 5/6891* (2013.01); *A61B 5/742* (2013.01); *A61B 5/0205* (2013.01); *A61B 5/1172* (2013.01); *A61B 5/1176* (2013.01); *A61B 2503/10* (2013.01)

(58) Field of Classification Search
CPC ....... A47C 7/744; A47C 7/723; A43B 3/0005; A43B 3/001; A43B 3/0015; A41D 13/0531; A42B 3/046; A42B 3/0473
See application file for complete search history.

(56) References Cited

FOREIGN PATENT DOCUMENTS

| JP | 2009106673 A | 5/2009 |
| JP | 2016087026 A | 5/2016 |

*Primary Examiner* — Timothy J Brindley
(74) *Attorney, Agent, or Firm* — Quinn IP Law

(57) ABSTRACT

A sport chair includes a seating surface operative to support a user and a processor. The processor is configured to detect the presence of a user on the seating surface, establish communication with an article of apparel on the body of the user, receive an indication of a physiological parameter of the user from a biometric sensor provided with the article of apparel, and output the physiological parameter to a display.

20 Claims, 10 Drawing Sheets

Related U.S. Application Data

(60) Provisional application No. 62/483,677, filed on Apr. 10, 2017, provisional application No. 62/513,411, filed on May 31, 2017.

(51) Int. Cl.
*A61B 5/0205* (2006.01)
*A61B 5/1171* (2016.01)
*A61B 5/1172* (2016.01)

SPORT CHAIR WITH GAME INTEGRATION

CROSS REFERENCE TO RELATED APPLICATIONS

The present application is a continuation of U.S. patent application Ser. No. 15/950,158, published as US 2018/0289166, which claims the benefit of priority from U.S. Provisional Application Nos. 62/483,677, filed Apr. 10, 2017, and 62/513,411, filed 31 May 2017. Each of the above-listed applications are incorporated by reference in their entirety and for all purposes.

TECHNICAL FIELD

The present disclosure relates generally to a chair with electronic aspects that are useful in a sporting or e-sporting environment.

BACKGROUND

Traditionally, athletes have utilized seating that performs the singular function of supporting the user. They then rely on ancillary, function-specific devices/solutions to meet other needs. In many cases, however, these function-specific devices/solutions either suboptimally address the user's needs, or they serve to inconvenience the user, and thus can run the risk of not being used to their full potential. As such, it is believed that there is a need for a seating solution that can support an athlete while providing ancillary functionality that may be situationally beneficial.

For example, it is well established that, during athletic activity, a person can perform better and at a lower risk of injury if their muscles are sufficiently warmed prior to engaging in the activity. It is common practice for athletes to warm their muscles prior to engaging in the activity by performing a low intensity exercise that increases both the metabolic activity and heat production within the muscles (i.e., "active warm-up"). It has been found that a typical period of active warm-up can increase the temperature of muscle by approximately 2-4° C. (i.e., from a resting temperature of from about 35-36° C. to an active temperature of from about 38-39° C.).

While many athletes do, in fact, perform some active warm-up in preparation for their athletic competition, it is also common for the athlete to experience some delay between their warm-up and the start of the competition. Likewise in team sports that involve player substitutions or breaks between periods of play, an athlete may break from the competition after competing for a period of time and sit/rest in a chair, such as shown in FIG. 1. These periods of inactivity may result in a cooling of the muscles that can lead to subsequent decreases in muscle performance and a heightened risk of injury.

The current state-of-the-art for maintaining muscle warmth during these periods of inactivity involves the athlete wearing thermally insulated apparel in an effort to minimize thermal losses to the ambient environment. The standard apparel does nothing to actively regulate muscle temperature at an optimal level. Moreover, insulating the entire body can have detrimental effects on the body's ability to regulate core temperature and the athlete's perception of comfort or fatigue, both of which can negatively impact long-term endurance.

In another example, it is common for players of many sports to interact with personal or team coaches when they break from the game. This collaboration can sometimes be verbal, either in person or over a telephone or other two-way communication device, and can use demonstratives, such as a dry-erase markerboard, pictures, or video displayed on a tablet or other computing device. In each instance, the communication means or demonstrative may fall short of conveying the intended message or information. Likewise, it involves heightened player engagement during a period when, for example, rest or recovery are also priorities.

SUMMARY

An embodiment of a sport chair with athletic integration includes a seating surface operative to support a user, a plurality of thermal transducers, a biometric sensor, and a processor. The plurality of thermal transducers are disposed on the seating surface, where each transducer is operative to at least one of: actively transmit thermal energy to the user, or actively sink thermal energy from the user. The biometric sensor is operative to monitor a physiological parameter of the user, such as at least one of hydration, weight, heart rate, respiration rate, or galvanic skin response. The processor is then in communication with each of the thermal transducers and with the biometric sensor, and is configured to control the plurality of thermal transducers to maintain a temperature of the user within a predefined temperature range, sense at least one physiological parameter of the user via the biometric sensor, and output the sensed physiological parameter to a display.

In an embodiment, the sport chair includes a processor that is configured to detect the presence of a user on the seating surface, establish communication with an article of apparel on the body of the user, and control the apparel to reduce a tension applied throughout the article of apparel. The sport chair may further include an inductive charging transmitter, where the processor may then be operative to charge a battery associated with the article of apparel by transmitting a magnetic field via the inductive charging transmitter.

Additionally, in an embodiment, the sport chair may include at least two of: thermal management means for regulating a temperature of the user; identity sensing means for determining an identity of the user; health sensing means for determining at least one biometric parameter of the user; apparel integration means for at least one of: charging a battery associated with an article of apparel on the body of the user; or controlling a tension applied through the article of apparel and against the body of the user; and display means for displaying an image within the field of view of the user.

DETAILED DESCRIPTION

Figure 2:
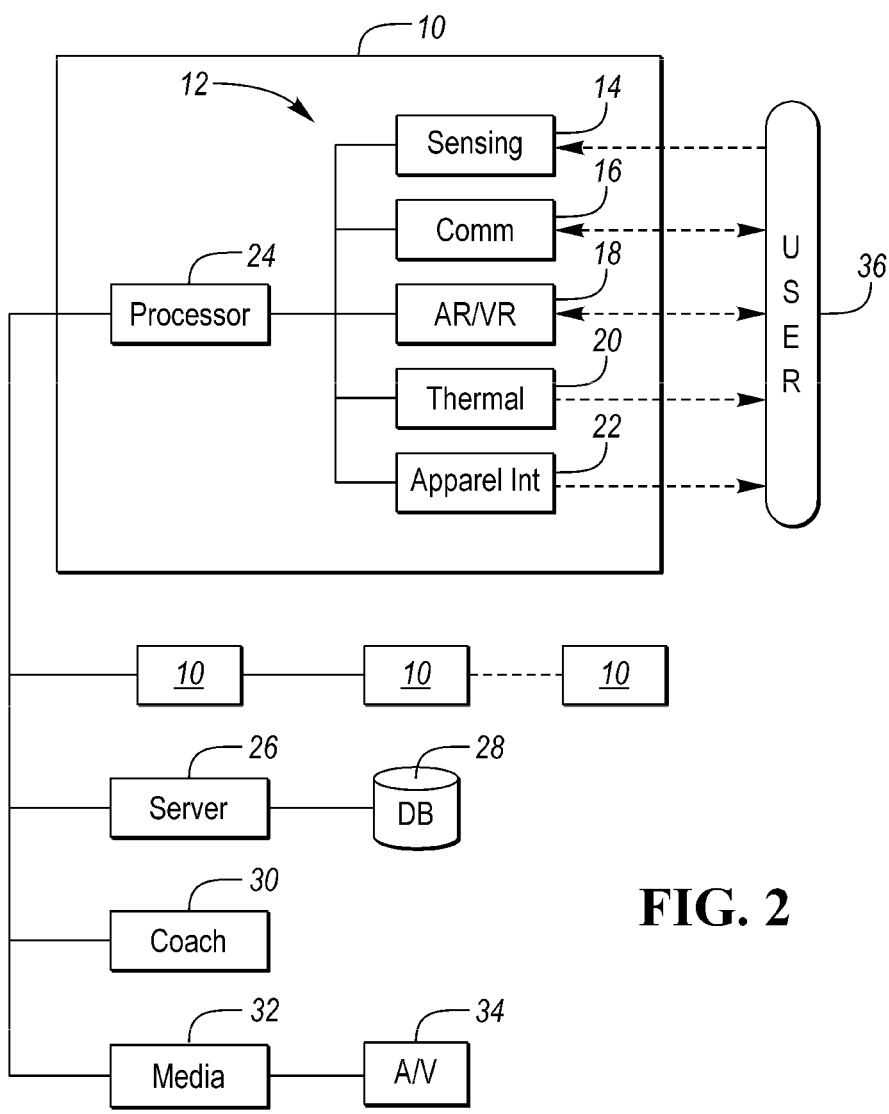
FIG. 2 is a schematic diagram illustrating an embodiment of a smart chair.

Referring to the drawings, wherein like reference numerals are used to identify like or identical components in the various views, FIG. 2 illustrates a schematic embodiment of a smart chair 10 that includes one or more integrated electronic aspects (generally at 12) that may be useful in a sporting or e-sporting environment. As shown, the chair 10 may include, for example, one or more sensors or sensing capabilities 14, bi-directional or uni-directional audio communication systems 16, a visual display system 18 such as an augmented or virtual reality display, one or more conductive and/or convective thermal transducers 20, and/or apparel integration capabilities 22. Each electronic aspect 12 may be directly controlled or in communication with a processor 24, which in some embodiments may be in remote communication with one or more other smart chairs 10, a remote storage server 26/database 28, a remote coaching terminal 30, and/or a media production device 32 that interfaces with external audio/visual (A/V) facilities 34.

Figure 3:
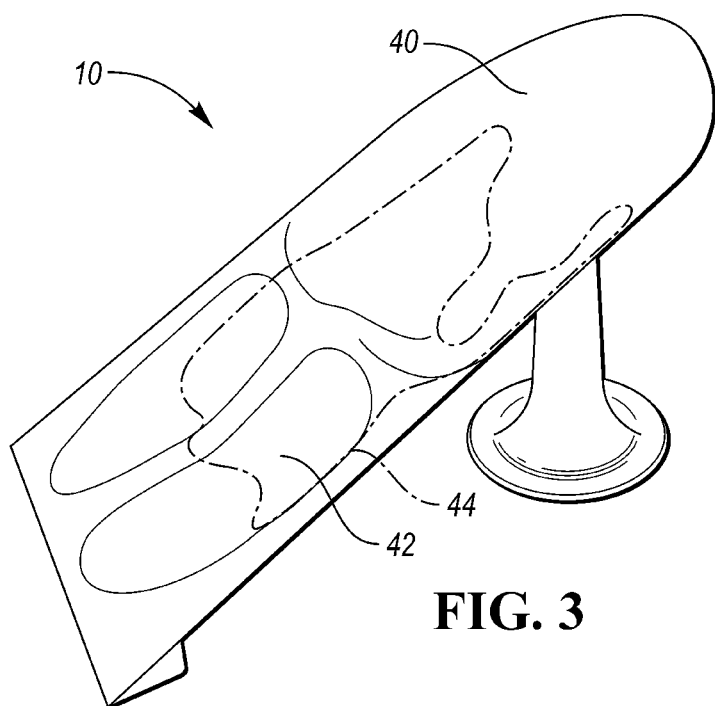
FIG. 3 is a schematic perspective view of an ergonomic chair having a rigid shell and a compliant seating surface.
Figure 4:
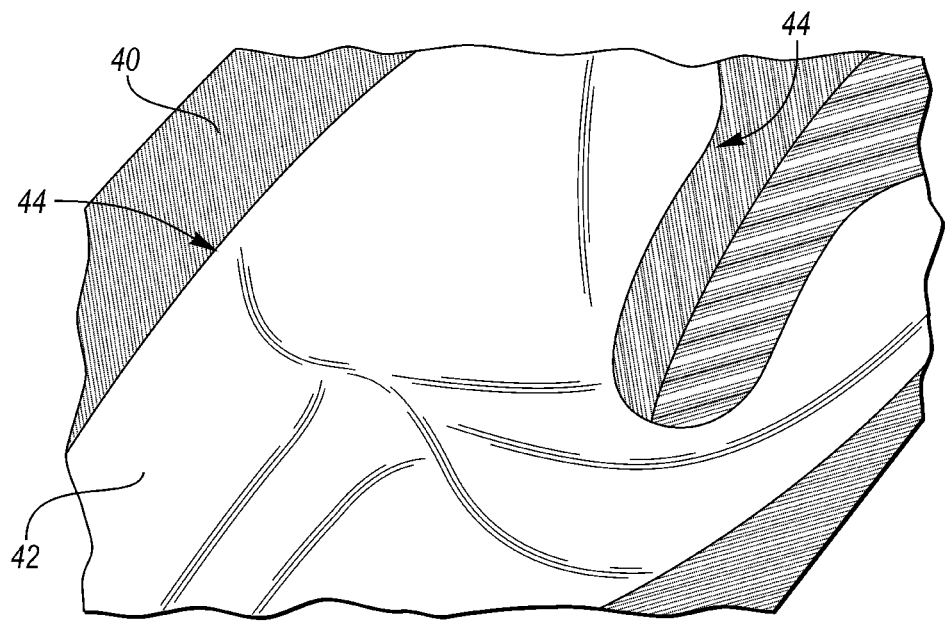
FIG. 4 is a schematic perspective view of a portion of the seating surface of the chair of FIG. 3.

From a structural perspective, it is desirable to construct the chair 10 to be as ergonomic as possible and designed to support the user 36 in a natural body pose that minimizes both average and maximum contact pressures between the user 36 and the chair 10. In some embodiments, an ideal, ergonomic chair design may include a mixed material construction that provides structure and form to the chair 10 while also serving to cradle the user 36 and maximize comfort. For example, in one configuration, such as shown in FIGS. 3-4, the chair 10 may include a rigid outer structure 40 that surrounds and supports a more compliant inner seating surface 42. In some embodiments, the rigid outer structure 40 may underlie the compliant inner seating surface 42, while in other embodiments, such as shown in FIGS. 3-4, the outer structure 40 and inner seating surface 42 may cooperate to define a continuous surface 44. The compliant inter seating surface 42 may be particularly configured to conform to the contours of the user's body when the user 36 sits within the chair 10. In this manner, the surface area that is in flush contact between the user 36 and the chair 10 is maximized.

Figure 1:
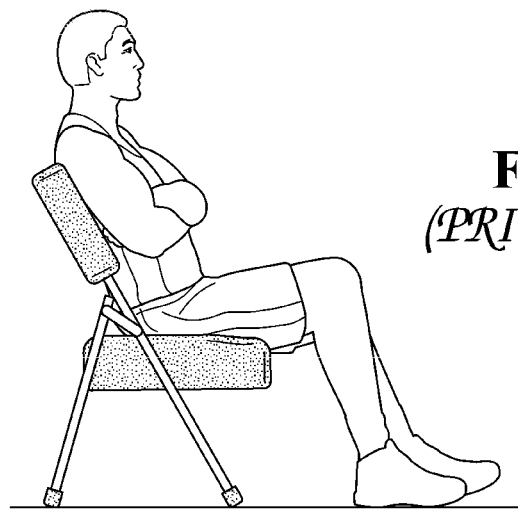
FIG. 1 is a schematic illustration of a user sitting in a prior-art athletic chair, such as may be used on the sidelines of a basketball game.
Figure 5A:
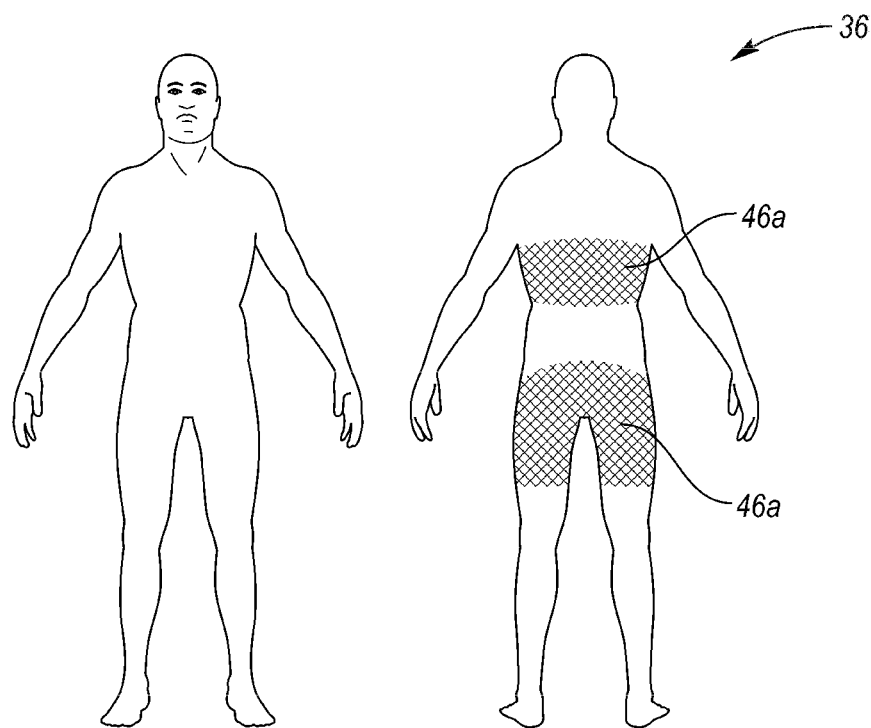
FIG. 5A is a schematic anterior and posterior view of a user, illustrating the contact area between a user and the prior art chair of FIG. 1.
Figure 5B:
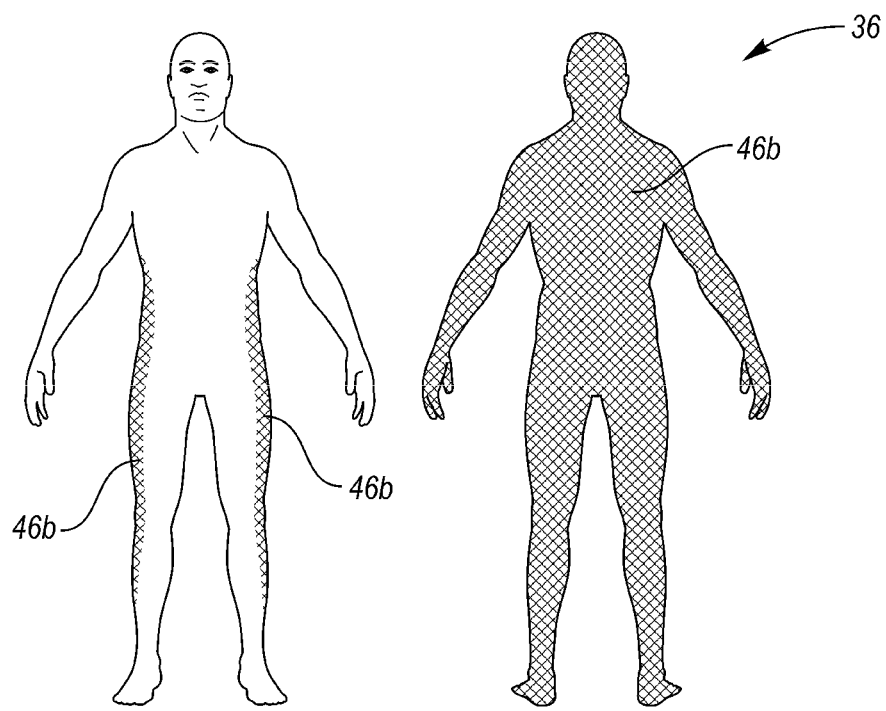
FIG. 5B is a schematic anterior and posterior view of a user, illustrating the contact area between a user and an ergonomic chair such as shown in FIG. 3.

FIGS. 5A and 5B schematically illustrate the differences in contact surface area between a chair such as shown in FIG. 1 and the chair 10 shown in FIG. 3. In FIG. 5A, it is clear that the traditional chair only establishes contact with the user 36 across a narrow surface area 46a of the mid-back and upper legs. Conversely, FIG. 5B illustrates an embodiment where the entire posterior surface 46b of the user 36 is in contact with the chair 10. By supporting more of the user, the chair 10 provides better ergonomics, and permits the user 36 to more completely relax into the chair and rest/recover if necessary. While FIG. 3 illustrates a somewhat reclined embodiment of the present chair, it may also be possible for the chair to be more upright or to assume other postures that provide improved contact pressures and ergonomic qualities above the standard folding chair of FIG. 1.

Figure 6:
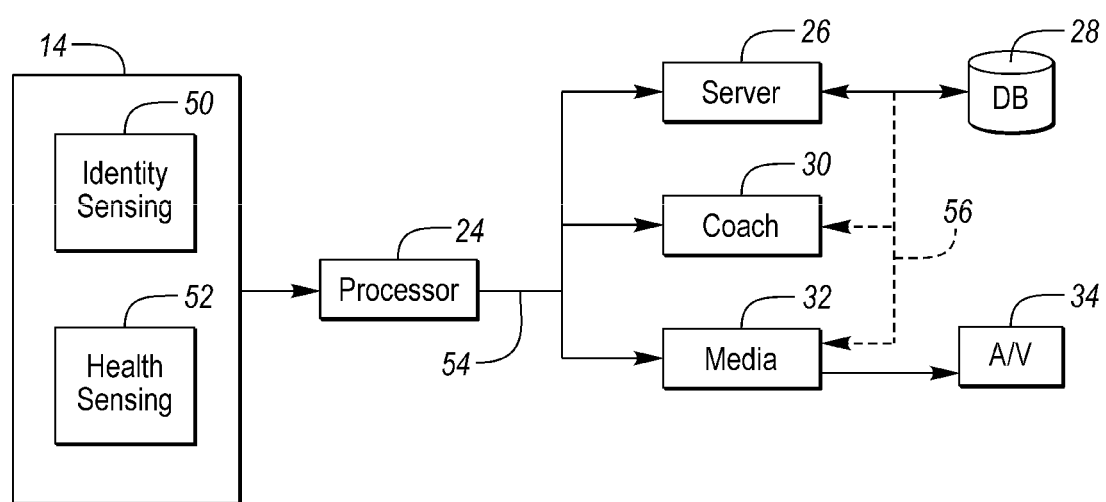
FIG. 6 is a schematic diagram illustrating sensory functionality embodied in a smart chair.

As schematically illustrated in FIG. 6, and also mentioned above, in some embodiments, the chair 10 may include various sensing capabilities 14 that aid in determining a user's identity (i.e., identity sensing 50) and/or the real-time health of the user 36 (i.e., health sensing 52). By knowing the identity of the individual in/on the chair 10, the processor 24 may customize certain performance attributes of the chair 10 to suit that user 36 and/or to coordinate other sensed data for third-party display and/or aggregation. Health sensing 52 may generally include the monitoring of certain biometrics, which may be useful in determining future game strategy (from a coaching perspective), establishing trends, and/or for third-party infographic display.

To enable identity sensing 50 the chair 10 may include an RFID reader for reading an RFID chip coupled with the user 36 or user's apparel, a camera equipped with facial recognition software, a finger print scanner, a keypad, or other such sensory means. Each of these identity-sensing modalities generally requires the chair 10 to sense some identifying attribute of the user 36. Once sensed, the respective sensor may convey information related to the attribute to the processor 24, which may draw the appropriate inference as to the user's identity.

In some configurations, health sensing 52 may include real-time monitoring of hydration, weight, heart rate, respiration, galvanic skin response, or other such biometrics. For example, in one configuration, the chair 10 may include one or more load cells to determine the real-time weight of the user 36. Given that rapid weight fluctuations are largely attributable to changes in hydration, if the processor 24 determines, via the load cell, that a user's weight has decreased by more than a predetermined amount or percentage throughout the course of the event, the processor 24 may conclude that the user 36 is dehydrated, and may alert the user 36 to drink fluid. Such an indication of dehydration may be provided, for example, by illuminating a light visible to the user 36 or visible to personnel in close proximity to the chair 10 (e.g., team personnel or training staff). As a different proxy for hydration, the processor 24 may further be configured to monitor changes in the weight of one or more water bottles, for example, via one or more strain gauges or load cells associated with a cup holder. In this manner, the processor 24 may track the total fluid intake of the user 36.

Likewise, in some configurations, the chair 10 may include one or more integrated sensors that are capable of determining the user's heart rate, respiration rate, and/or galvanic skin response. These sensors may include one or more electrodes, load cells, strain gauges, light emitting diodes, optical sensors, or other such sensors that may be known to monitor such parameters. Furthermore, these sensors may be integrated within the surface of the chair, underneath a moisture barrier layer, and/or underneath a cushioning layer. In other embodiments, as further described below, one or more of the sensors may be embedded in the user's apparel and/or in a wearable device or strap in direct communication with the user's skin.

Figure 7:
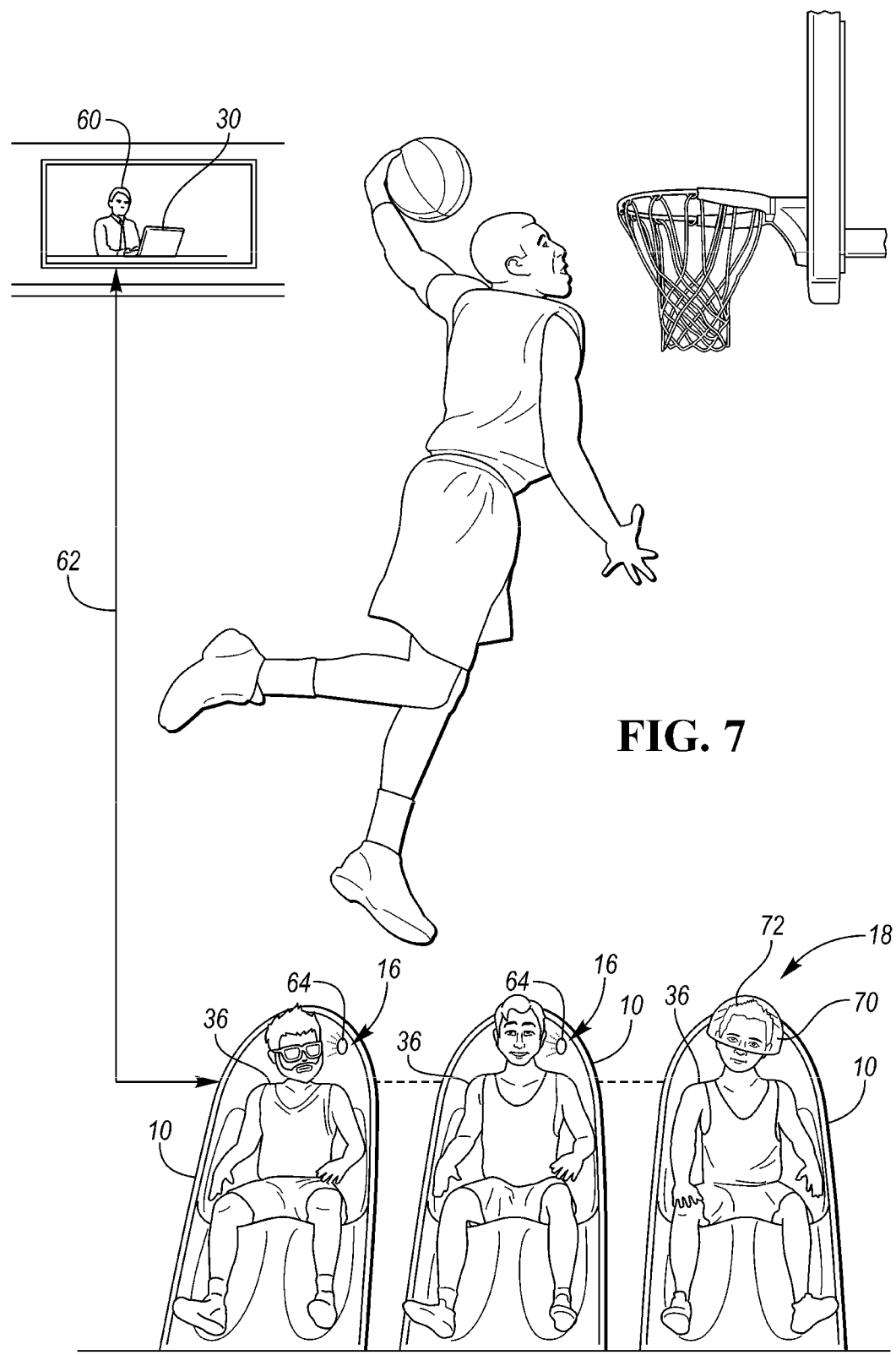
FIG. 7 is a schematic perspective view of a basketball court including a plurality of users each sitting in a smart chair.

Once coordinated with a user's identity, the player-specific health data 54 may then, for example, be logged or recorded by the server 26 and/or by an associated database 28 for the purpose of trend analysis and real-time detection of trend deviations. Furthermore, the real-time health data 54 and/or trend data 56 may then be streamed to a remote coaching terminal 30 (such as generally shown in FIG. 7), and/or a media production device 32, where it may be displayed for informational purposes. For example, in some embodiments, coaching/training staff may use the player-specific health data 54 to make assessments regarding whether the user 36 is sufficiently rested/recovered to resume competition. Likewise, media production staff may incorporate the player-specific health data 54 and/or trend data 56 into a live or televised audio/visual broadcast (e.g., via A/V facilities 34). In still other embodiments, the health data 54 and trend data 56 may be presented directly to the user via a display.

In yet another embodiment, player-specific health data 54 and/or trend data 56 may further be used in an e-sports context as part of the game play. For example, a user's real-time sensed physiologic response during a game may be used as an input to control visual focus and/or controller sensitivity or jitter. In such an embodiment, tense or stressful encounters (as assessed, for example, by heart rate or respiration rate) may result in a less-focused display, loss of a degree of peripheral vision, or increased jitter in the controls. As such, a gamer that is able to control their physiological response may have an advantage.

As schematically illustrated in FIG. 7, and also mentioned above, in some embodiments, the chair 10 may include various audio communication systems 16 that aid in facilitating audible communication between two or more users 36 and/or between one or more users 36 and local or remote coaching staff 60 (i.e., over a data connection 62). In such an embodiment the audio communication systems 16 may include at least a speaker 64 provided in connection with each respective chair 10. Likewise the audio communication system 16 may further include at least one microphone or other audio input device associated with a remote coaching terminal 30 and/or one or more of the provided chairs 10. In this manner, the audio communication systems 16 may facilitate player-to-player communication and/or communication between users and coaching staff. Player-to-player communication may be particularly beneficial in noisy stadium/arena environments, or in sports where players are constrained to sit in a linear arrangement. Likewise, coach-to-player communication may better enable in-game adjustments by facilitating player-specific or team strategy advice to any one or more users 36 or groups of users 36.

In some embodiments, the speaker 64 and/or audio communication system 16 may be operative to provide a noise cancellation function to each respective user 36. Such a noise cancelling capability may be useful in loud arenas or stadiums to provide the user 36 with both a sense of calm and relaxation, as well as to better facilitate communications between players and between players and coaching staff In such an embodiment, the chair 10 may be provided with a microphone that receives audible background/stadium noise. The processor 24 may receive the signal from the microphone, and direct the speaker 64 to broadcast an out of phase audio wave to the user 36 that destructively interferes with and/or lessens the magnitude of the ambient noise. In some embodiments, this may be better provided for with a chair 10 having a wraparound head support.

In addition to purely audio communication/advice, many athletes rely on visual information and/or demonstratives to better understand in-game strategy and tendencies of the opposing team. As such, in some embodiments, the smart chair 10 may include a visual display system 18 that may incorporate an augmented reality (AR) field of view and/or one or more immersive or partially immersive displays (e.g., akin to virtual reality (VR)). These display systems 18 may be used by coaching staff to replay previous game sequences, to diagram future game sequences, to provide overhead and/or perspective views of live and/or recorded play, to enhance a user's real-time view of live play. Furthermore, in some embodiments, the visual display system 18 may be used to relax a user 36 following a period of strenuous activity and/or may be used to energize a player before entering the game/competition.

Specifically, as shown in FIG. 7, in some embodiments, the visual display system 18 may include a graphical display 70 that may be worn on or over a portion of the user's head 72, and particularly in front of the user's eyes. In some embodiments the display may be embodied in a helmet, visor, or other head covering element associated with the chair 10. Alternatively, the display 70 may be embodied in glasses, goggles, or other discrete lenses that may be separate from the chair 10. In either embodiment, it may be preferable for the graphical display 70 may include a discrete visual display for each of the user's eyes (or capabilities to project stereoscopic visuals separately to each eye) in order to provide a stereoscopic display to the user 36.

In an AR configuration, the graphical display 70 may include a substantially transparent lens that is operative to provide one or more visual elements within the field of view of the user 36. The display 70 may include, for example, a transparent lens that receives a projected image from an adjacently positioned projector, a selectively emitting display (e.g., an OLED display), and/or a display that can selectively alter light transmission (e.g., an LCD). Furthermore, the graphical display 70 may include a view-tracking system that can detect and/or understand the user's real-time field of view by looking outward, such as using a camera, looking inward to track the user's eye motion, and/or by understanding the real-time position and orientation of the display 70. Examples of graphical display technology that may be used with the present system for Augmented Reality presentation are detailed in U.S. Patent Application No. 2014/0160001, which is incorporated by reference in its entirety.

In a VR configuration, the graphical display 70 may generally be non-transparent such that the display blocks the user's perception of their surroundings external to the display. In such an embodiment, the display 70 may include, for example, a projected display on an opaque or translucent surface, an emitting display with an opaque back-surface, or a backlit, selectively transmissive display such as an LCD or LED display. In some embodiments, VR and AR may be accomplished using the same device, and/or selectively over discrete portions of the device, for example, using a selectively dimmable electrochromic layer disposed behind an emitting display such as an OLED display. An example of such a combined VR/AR display is described in U.S. Patent Application No. 2016/0055822, which is incorporated by reference in its entirety.

Figure 8:
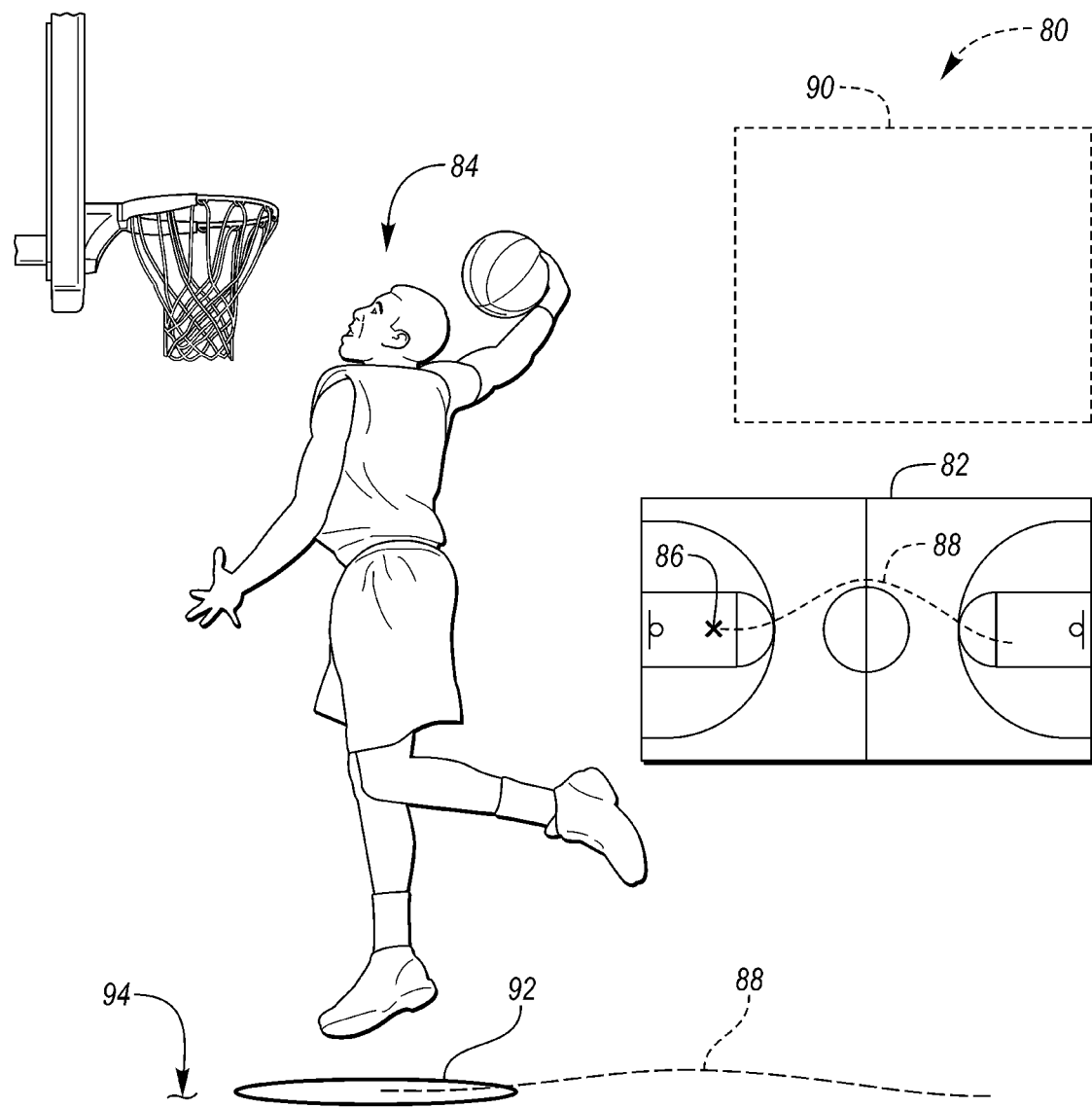
FIG. 8 is a schematic mixed-reality field of view of a user of FIG. 7, illustrating both augmented and virtual reality display aspects.

FIG. 8 schematically illustrates an embodiment of a mixed-reality view 80, such as may be seen through the graphical display 70 shown in FIG. 7. In this embodiment, a diagrammatic view 82 of the court is overlaid within the user's real-time field of view 84 to more accurately illustrate player movement that lead to the current live action. More specifically, in some embodiments, this top view of the court may illustrate all player positions using either live images or diagrammatic symbols 86, and may further include player history lines 88 to represent player motion for a predetermined amount of preceding time. In some embodiments, the view 80 may be dynamically reconfigurable, and may allocate a portion of the view 80 for replay video (i.e., replay window 90), which may selectively be fed to the display 70 via the coaching terminal 30. Additionally, in some embodiments, the display 70 may superimpose a position indicator 92 coincidently with or marginally above the floor 94 to highlight real-time player position. Similar to the diagrammatic view 82, player history lines 88 may trail the position indicator 92 to illustrate player motion. During time outs, for example, the relative sizing of the diagrammatic view 82 and/or replay window 90 may be adjusted/enlarged to provide enhanced coaching and strategy illustration.

While FIGS. 7-8 illustrate the use of audio and video capabilities 16, 18 in connection with the sport of basketball, they may be readily suited for other sports and e-sports as well. For example, the current state of the art for in-game coaching in the sport of American Football includes small groups of players collectively reviewing printed images and/or replay video provided on tablet displays. The present chair technology would provide a significant benefit to coaching and team integration while enabling the players to relax in a seated manner while focusing on the coaching advice. Furthermore, as noted above, the present chair 10 may include a plurality of thermal transducers 20 for maintaining the athlete's body in a ready state (which is typically not possible if players are required to huddle around a singular display). In an e-sporting context, the audio and video capabilities 16, 18 may be used to provide an immersive and/or semi immersive environment for the gaming competitor, while enabling the competitor to outwardly communicate and/or for the competitor's personal commentary to be broadcast to a larger audience.

Figure 9:
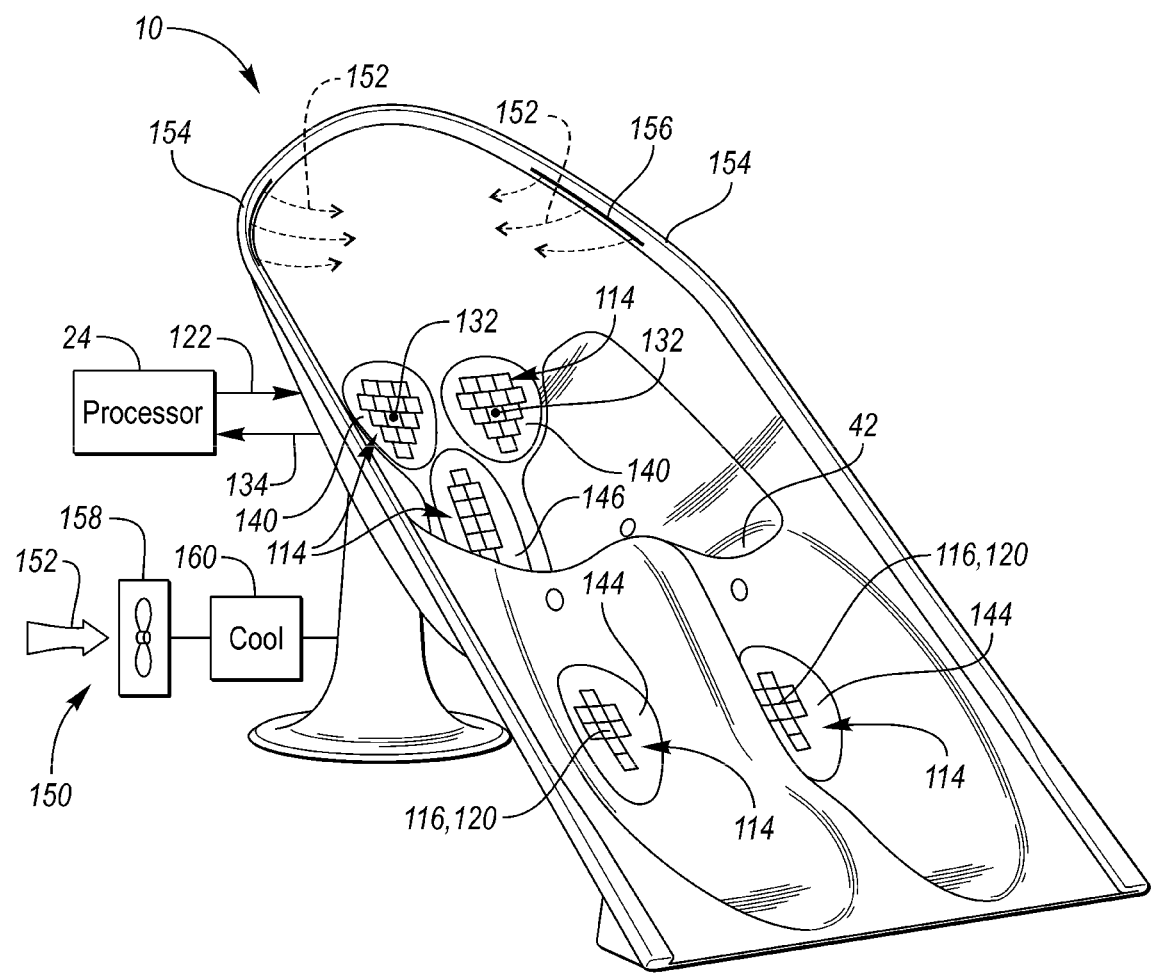
FIG. 9 is a schematic perspective view of an embodiment of a smart chair with thermoregulating capabilities.

In a traditional sporting context, FIG. 9 schematically illustrates an embodiment of a smart chair 10 with a plurality of thermal transducers 20 that are configured to actively maintain the temperatures of various muscle groups within the user's body in a "warmed-up" state, and one or more systems that are adapted to aid in reducing/regulating the user's core body temperature and/or lessening feelings of fatigue/exhaustion.

Figure 10:
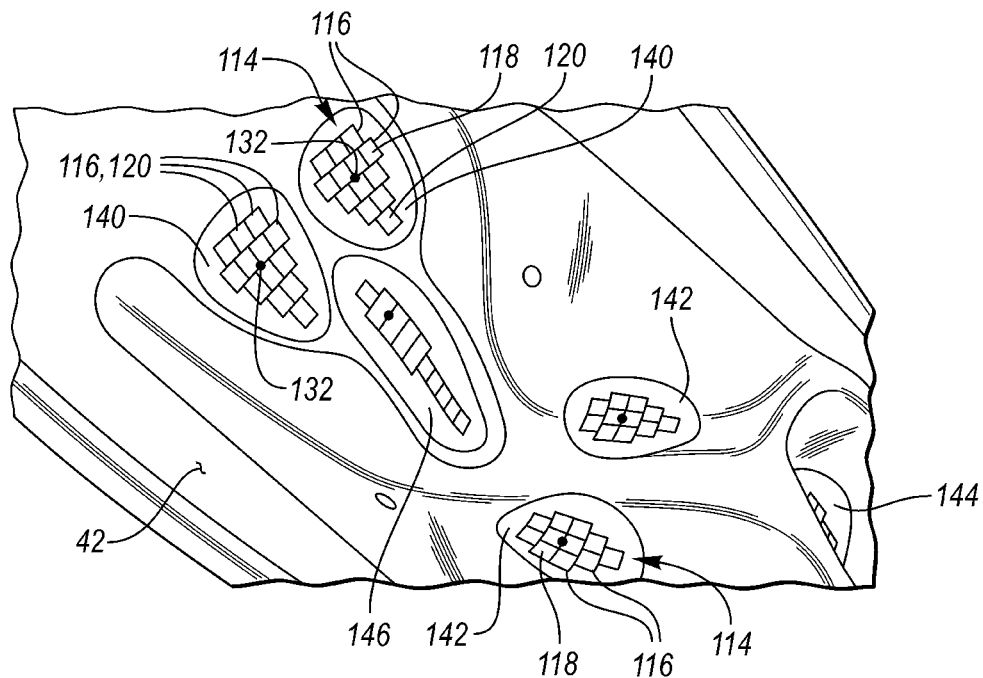
FIG. 10 is a schematic perspective view of a portion of the seating surface of the smart chair of FIG. 9.

As shown in FIGS. 9-10, in some embodiments, the inner seating surface 42 of the chair 10 includes a plurality of discrete thermal zones 114 that are each adapted to actively apply heat and/or apply cooling to the user 36 via conductive heat transfer. As used herein, "applying heat" or "heating" involves controlling the respective thermal zone 114 to generate and outwardly transfer a thermal flux to the user 36 (i.e., a heat source), whereas "applying cooling" or "cooling" involves controlling the respective thermal zone 114 to absorb and inwardly receive a thermal flux from the user 36 (i.e., a heat sink).

Each thermal zone 114 includes one or more working elements 116 that are configured to actively generate and/or absorb thermal energy, and a user-facing contact surface 118 that facilitates heat transfer between the working element 116 and the user 36. In one configuration, such as better shown in FIG. 10, the working element 116 may be, for example, a thermoelectric cooler, such as a Peltier device 120, and the contact surface 118 may include the user-facing outer surface of the Peltier device 120. As is well understood in the art, Peltier devices are solid-state devices that can controllably vary a temperature gradient across a thickness of the device 120 in response to an applied electric current 122 (schematically shown in FIG. 9). Beneficially, these devices 120 can be used to either heat or cool a desired surface. For example, if a current is applied to the Peltier device 120, the contact surface 118 may thermally heat while an opposing side may thermally cool. Conversely if an opposite current is applied to the Peltier device 120, the contact surface may thermally cool while an opposing side may thermally heat.

To maximize the flexibility and utility of the chair 10, it is preferable for each thermal zone 114 to be capable of both applying heat and applying cooling to the user, such as may be provided by a Peltier device 120. Given this versatility, the chair 10 may be used to actively warm-up a user 36 prior to an event, maintain the user 36 in a state of readiness during breaks in the event, and/or cool down the user 36 after the event simply by altering the heating/cooling profile across the various thermal zones 114.

In other embodiments, select zones may be configured strictly to apply heat (e.g., such as zones that are dedicated for warming muscles), while other zones may be configured strictly to apply cooling (e.g., zones for cooling/aiding to regulate the user's core temperature). Dedicated heating zones may utilize a working element 116 such as, for example, a resistive heating element or a bladder filled with a heated liquid. Likewise dedicated cooling zones may utilize a working element 116 such as, for example, an air-cooled heatsink, a refrigeration system, or a cryogenic fluid, a bladder filled with a cooled liquid. In a further embodiment, a dedicated cooling zone may incorporate the use of a large mass with a high thermal capacity held at a temperature lower than the user's skin (e.g., a large block of steel, aluminum, or vessel of water).

In order to maintain a user 36 at an optimal state of athletic readiness, the chair 10 is operative to independently and selectively control the temperature output of each of the plurality of thermal zones 114. By doing so, the chair 10 may attempt to regulate different local areas of the user's body at their respective optimal temperatures. To accomplish this independent and selective control, the processor 24 may be in communication with each of the plurality of thermal zones 114. The processor 24 is configured to execute one or more software/firmware algorithms stored thereon, or readily accessible thereto to understand and independently control the temperature of each respective thermal zone 114.

In one configuration, the processor 24 may control the temperature of each respective thermal zone 114 in an open loop manner. For example, the processor 24 may receive an indication of a desired amount of thermal flux for each zone 114, and may operate the respective working elements 116 to respond accordingly. In a system where the working element 116 is a Peltier device 120, the processor 24 may directly supply a current 122 to each device 120 in response to the received indication of desired thermal flux. The received indication of desired thermal flux may be a qualitative measure of a desired amount of heat/cooling that should be applied via the zone 114, and may be input by the user 36 via one or more digital or analog input devices. Alternatively, the desired amount of thermal flux may be preprogrammed into the processor 24 based on the desired use of the chair 10 (e.g., according to the sport, athletic intensity, sporting environment, and/or the anticipated duration of the rest).

While open loop temperature control presents an easily implemented solution, a more preferred strategy involves the use of closed loop temperature control. In a closed loop temperature control strategy, each thermal zone 114 may include one or more temperature sensors 132 that are operative to output a signal 134 indicative of the temperature of the contact surface 118 and/or the temperature of the user 36 immediately proximate to the contact surface 118. With this feedback, the processor 24 may modulate the output of the working element 116 (e.g., by varying the current 122 provided to the working element 116) in an attempt to minimize the difference between the sensed temperature and a specified set point temperature. In one configuration, the user 36 may directly input their desired temperature set point for each respective thermal zone 114. In another configuration, the set point temperatures may either be automatically selected by the processor 24 or may be preprogrammed into the processor 24 according to the nature of the sport and the environment in which the sport is played.

In a preferred embodiment, the processor 24 may automatically attempt to provide optimal thermal relief to the user, while attempting to maintain the user's various muscle temperatures at their respectively optimal levels for the activity that the user 36 is participating in. To accomplish this, the thermal zones 114 are desirably located such that they align with and directly contact the user 36 at or near the muscle group and/or body region that they are intended to apply heat or cooling too. For example, if the chair 10 is used in connection with the sport of basketball (e.g., for use before the start of a game, or following a player substitution), thermal zones 114 may desirably be placed to contact and be in direct thermal communication with the user's gluteal muscles, muscles of the hamstring (i.e. semitendinosus, semimembranosus, and/or biceps femoris), and/or the muscles of the calf (i.e., gastrocnemius). It may also be beneficial to place thermal zones 114 for direct contact with muscles of the back (i.e., trapezius, rhomboideus, erector spinae, serratus, abdominal obliques, and/or latissimus dorsi), shoulders (i.e., deltoids) and/or arms (e.g., triceps).

For the purpose of maintaining muscle temperature at an optimal level, FIGS. 9-10 schematically illustrate a first plurality of thermal zones 140 that are positioned for direct contact with the upper back (e.g. the rhomboid muscles), a second plurality of thermal zones 142 that are positioned for direct contact with the gluteal muscles and/or the muscles of the hamstring, and third plurality of thermal zones 144 that are positioned for direct contact with the muscles of the calf. In each instance, it is desirable for the processor 24 to maintain the respectively adjacent muscles at a temperature that is from about 2° C. to about 4° C. above their natural resting temperature, which may be achieved by controlling the temperature of the contact surface 118 to a set point temperature it is at or marginally above the desired muscle temperature.

While maintaining muscles at an elevated temperature can be useful in maintaining the muscles in a state of readiness, which both reduces the likelihood of future injury and improves muscle performance/power, heating can be detrimental to the longer-term endurance of the athlete and to the psychological perception of thermal relief following a period of exertion. Therefore, in an effort to alleviate fatigue, enhance user comfort, and reduce thermoregulatory stress within the user's body, the present chair 10 can apply cooling to the user 36 in one or more of a variety of forms.

First, the chair may include a thermal zone 146 aligned with the user's spine and/or neck that is configured to actively sink thermal energy from the user 36. The neck and spine regions carry a significant amount of blood flow, yet have minimal amount of muscle mass that are at risk of cramping or negatively affecting athletic performance if cooled. As such, by applying cooling the spine and/or neck, the chair 10 may aid the user's body in managing its core temperature (i.e., lessening the thermoregulatory strain experienced by the body), while also providing psychological benefits such as the feelings of rest, recovery, and/or thermal relief. In one configuration, applying cooling to the spine and/or neck may be performed in a controlled manner to avoid any adverse effects on muscle temperature even despite the application of external heating.

Figure 11:
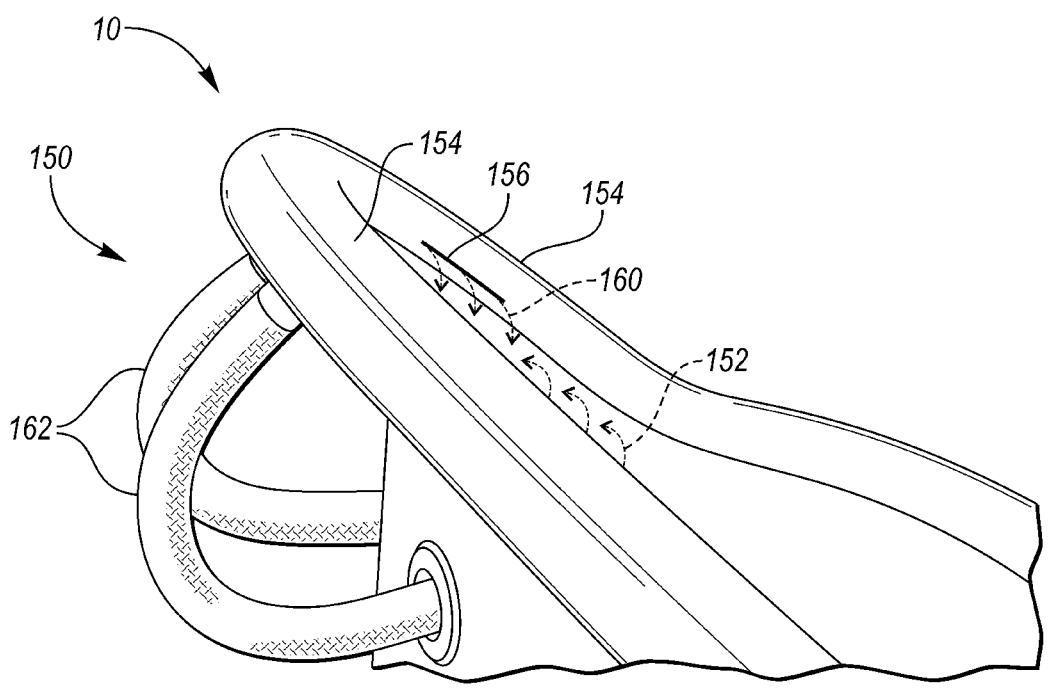
FIG. 11 is a schematic side view of a portion of a convective head cooling system, such as may be used with the smart chair features of FIG. 9.

The chair 10 may further provide cooling to the user 36 by way of a convective cooling system 150 that directs airflow 152 at and across the head and/or face of the user, such as schematically shown in FIGS. 9 and 11. While it is uncertain whether convective cooling of the head and/or face has a significant impact on core body temperature, it has been shown to provide the beneficial effects of prolonging the average time to fatigue and reducing the user's perceived level of total exertion. Furthermore, it has been found that in some circumstances, cooling of the face can have distinct performance advantages during aerobic activity.

As shown in FIG. 9, and more clearly in FIG. 11, in some embodiments, the convective cooling system 150 may include an air plenum 154 that is configured to direct airflow 152 at the head and/or face of the user 36. In one configuration, the air plenum 154 includes one or more orifices, slots, or other such vents 156 that permit pressurized air to exit the plenum 154 and be directed toward the head/face of the user 36. In one configuration, it may be preferable for the air to be delivered in a laminar manner, which may enable the exiting airflow 152 to closely follow the contours of the user's head and face. While it is preferred for the one or more orifices, slots, or other such vents 156 to be located sufficiently forward relative to the user's head (e.g., anterior to the coronal plane) for the airflow 152 to be directed across the user's face, in some embodiments, the nature of the flow (e.g., laminar/boundary following) may enable face cooling even if the vents 156 are located further rearward.

As schematically shown in FIG. 9, the convective cooling system 150 may further include one or more fans 158 or other blower devices configured to move air within the system 150. For the purpose of cooling the airflow 152 prior to directing it at the user, the convective cooling system 150 may further include one or more refrigeration devices 160 that are disposed within the path of the air prior to the air exiting the vents 156. In one configuration, the refrigeration device 160 may utilize, for example, refrigerant or evaporative cooler to cool the flowing air. In another configuration, the refrigeration device 160 may utilize and/or include the reverse surface of one or more of the Peltier devices 120 that are being used to warm the user's muscle. Finally, as shown in FIG. 11, the convective cooling system 150 may further include any required ducting 162 that is needed to carry airflow from the fan 158 to the plenum 154.

In some embodiments, the chair 10 may further include a convective humidity management system that is operative to manage the humidity within the microclimate immediately surrounding the user 36. For example, following a period of intensive activity, the user's body may be exceedingly covered in sweat. The humidity management system may direct airflow around the body of the user 36 in a manner that leads to the evaporation of the sweat and/or aids in in reducing any increase in local humidity that is attributable to evaporated sweat. The humidity management system may utilize the plenum 154 and/or micro channels extending through the inner seating surface 42 of the chair 10 to direct a flow of air over the user's body. In one configuration, the body-directed airflow may be heated (e.g., via a heating element) to avoid having a noticeable chilling effect on the user's skin/muscles. Alternatively, in some embodiments, the body-directed airflow may be at an ambient temperature or cooled below an ambient temperature in an effort to cool the user 36 (if so desired) and/or to provide a psychological benefit of being refreshed.

In a configuration where a particular seating surface 42 is likely to receive a plurality of different users throughout the athletic event, it is of particular importance for the chair to have sufficient compliance to comfortably and ergonomically receive users having differing body types. Likewise, the plurality of thermal zones 114 should be located such that they contact the desired muscle groups/body locations for a range of body types/sizes.

To provide the most optimal thermoregulatory effect across a plurality of different users/body sizes, in one configuration the plurality of thermal zones 114 may be dynamically assigned and/or constructed based on an understanding of the user's specific anatomy. For example, a plurality of discrete working elements 116 may be disposed across the entire inner seating surface 42 of the chair 10 (or across a substantial portion thereof). Upon receiving the user 36 into/onto the chair 10, the processor 24 may intelligently define the plurality of thermal zones 114 by grouping adjacent sets of working elements 116 according to that user's specific anatomy.

In one configuration, the processor 24 may determine the user's anatomical makeup by monitoring the contact pressure between the user 36 and the chair 10, for example, using a plurality of strain gauges or load cells integrated into the seating surface 42 and/or working elements 116. In another configuration, the processor 24 may determine the user's anatomical makeup by receiving an indication of the user's identity (e.g., via identity sensing 50 capabilities), and then retrieving that user's anatomical proportions from an electronic database.

In yet another configuration, instead of full dynamic construction of the thermal zones 114, certain predefined thermal zones 114 may be selectively modified if a user's anatomy dictates such modification. For example, as shown in FIG. 10 the different thermal zones 114 maybe sized/located to accommodate users at both large and small ends of the expected user 36 size (e.g., $95^{th}$ and $5^{th}$ percentile anatomy). If a particular user's anatomy does not require the entire array, individual working elements 116 may be selectively deactivated upon the processor 24 learning the user's identity.

Referring again to FIG. 2, in some embodiments, the chair 10 may include one or more electronic aspects that integrate with a user's footwear or apparel (i.e., apparel integration 22). For example, if the user 36 is wearing shoes or apparel with auto tensioning mechanisms, then the chair 10 may cause the user's shoes/apparel to relax when the user 36 initially sits down, and re-tension when the user 36 is about to enter/re-enter competition. Examples of auto-tensioning footwear and apparel are described in U.S. Pat. Nos. 8,046,937 and 9,365,387, which are hereby incorporated by reference in their entirety. Such devices may generally operate by electronically spooling or constricting one or more tensioning fibers provided within the article. As the fibers are drawn in, they may cause the article to apply a generally constrictive force to a portion of the user's body. While this force can be beneficial during competition, it can sometimes be perceived as uncomfortable when the user 36 is attempting to relax.

Figure 12:
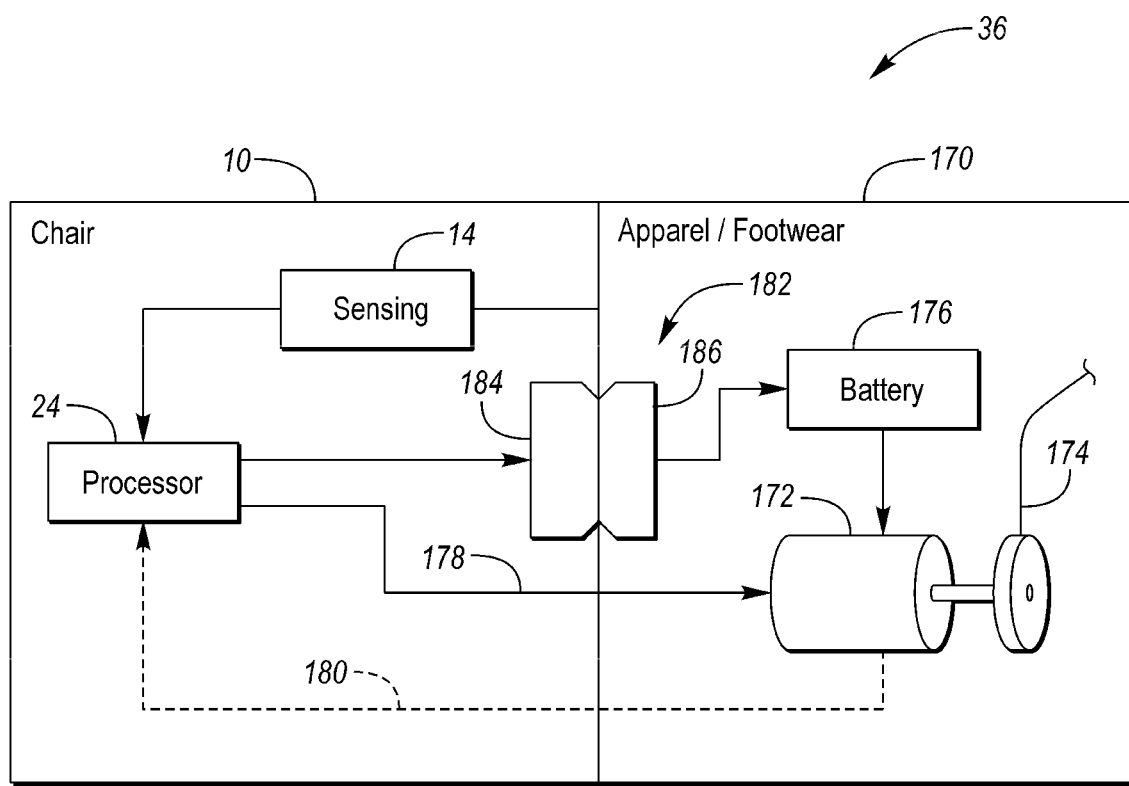
FIG. 12 is a schematic diagram illustrating an embodiment of a smart chair with apparel charging and auto-tensioning capabilities.

FIG. 12 schematically illustrates one embodiment of an apparel integration schema. As shown, the chair 10 is in close contact with an article of apparel and/or footwear 170 (generally "apparel 170") that is being worn by a user 36. The apparel 170 includes a motor 172 (or other electrically actuated constriction element, such as shape memory alloy, electroactive polymers, or the like) that is operative to selectively tension at least one fiber 174 provided in the apparel 170, wherein tensioning or relaxing the fiber 174 causes the apparel 170 to constrict or relax about the user 36. Examples of apparel 170 that may utilize such selective constriction includes compression shirts, compression arm or leg sleeves, compression shorts, knee braces, wrist braces, ankle braces, foot braces, gloves abdominal padding/braces, shoes, and the like. In some embodiments, the motor 172 may be powered by a battery 176 or other charge storing device that is carried by the apparel 170. In other embodiments, the motor 172 may be powered by an external source, such as the chair 10 and/or processor 24.

Upon a user 36 sitting into the chair 10, the processor 24 may detect the user's presence and/or identity via the sensing capabilities 14 integrated into the chair 10. Following this indication, the processor 24 may direct the motor 172 to unspool and/or relax the tension on the fiber 174, thus causing the apparel 170 to lessen any constriction about the user 36. The processor 24 may provide this instruction via a data connection 178 between the chair 10 and the apparel 170. In some embodiments, this data connection may be a wired data connection that is made between electrical terminals on the chair 10 and mating electrical terminals integrated into the apparel 170. Such terminals may include, for example, magnetic contact elements to aid in ensuring contact. In other embodiments, the data connection 178 may involve low power Bluetooth radios, near field communication capabilities, or other short-range wireless digital communication means.

When a user 36 is ready to resume play and/or stand up from the chair 10, the processor 24 may direct the motor 172 to re-tension the fiber(s) 174 to cause the apparel 170 to re-constrict about the user 36. In one embodiment, the processor 24 may understand the user's intentions to exit the chair 10 after receiving an exit command from the user 36 (e.g., the user 36 pressing a button indicating re-tension or exit). In another embodiment, the processor 24 may understand the user's intentions to exit the chair 10 by monitoring the user's body posture and/or contact pressures between the user 36 and the chair 10 and inferring an immanent attempt to stand. In still another embodiment, the apparel 170 may operate autonomously to re-tension following a break in communication or contact with the chair 10 (i.e., when the user fully stands from the chair 10).

As further illustrated in FIG. 12, in some embodiments, the processor 24 may receive a tension feedback signal 180 from the motor 172 indicative of the real-time tension through the fiber 174 and/or apparel 170. The processor 24 may use this signal 180 to ensure the apparel 170 is adequately relaxed upon sitting, and to adaptively re-tension the apparel 170 when the user 36 is ready to resume competition. In some embodiments, adaptive tensioning may be useful to account for swelling, fluid retention, and/or changes in a user's body proportions that may occur during the competition. Said another way, if tensioning based on, for example, exerted apparel pressure against the user, the absolute size of the apparel 170 may be different at the start of the competition than at the end of the competition due to changes in body size.

With continued reference to FIG. 12, in some embodiments, the apparel integration 22 features of the present chair 10 may include charging capabilities 182 for an adaptive article of apparel and/or footwear 170. In some embodiments, these capabilities may include an inductive charging means that includes an inductive charging transmitter 184 provided on the chair 10, and an inductive charging receiver 186 associated with and/or integrated into the apparel 170. Examples of suitable charging capabilities are further described in U.S. Pat. No. 8,058,837 and U.S. Patent Application No. 2016/0345654, both of which are incorporated by reference in their entirety. The chair 10 may utilize the time that the user 36 is sitting in the chair 10 to ensure the battery 176 is at an adequate state of charge. If charging is required, the chair 10 may transmit a magnetic field from the inductive charging transmitter 184 that may be received by the inductive charging receiver 186 and used to replenish the stored charge in the battery 176.

In some embodiments, the sensing capabilities 14 described above with respect to FIGS. 2 and 6 may be incorporated with the apparel integration 22 functionality. More specifically, the user's apparel may include one or more sensors that are held in close proximity with or in contact with the skin of the user 36. These sensors may include, for example, heart rate sensors, respiration sensors, galvanic skin response sensors, RFID identity indicators, and the like. The sensors may be integrated/woven into one or more compression-fitting garments, protective padding, footwear, straps worn around the torso or other appendages, or adhesively stuck on to the user 36 (generally "apparel sensors"). In some configurations, the apparel sensors may include a memory device, such as a flash or EEPROM memory that can record periodic user data while the user 36 is engaged in the athletic competition. When the user 36 sits on the chair 10, the chair 10 may communicate with these apparel sensors in a uni-directional or bi-directional manner (e.g., low power Bluetooth, NFC, etc) to receive real time user biometric information and/or biometric information that has been stored to the memory of the apparel sensor. This downloadable content may be used in the same manner as biometric data that is directly acquired by the chair 10, as described above.

In some embodiments, the apparel-based sensing capabilities may include one or more accelerometers that are embedded within a user's protective padding and/or woven or otherwise integrated with the user's compression-based undergarments. Such sensing capabilities may be useful in recording the magnitude and location of any impacts or collisions that may occur during the competition. Upon the user exiting the field of play and sitting on the chair 10, the recorded sensory data may be downloaded by the processor 24 and/or capabilities within the chair 10. In such an embodiment, requiring close contact between the sensing electronics and the receiver may provide for lower weight and lower power additions to the apparel, which may receive greater athlete acceptance and lead to a greater adoption.

While the chair 10 described above provides benefits for an individual athlete, in some configurations, a sports team may find particular utility in providing similar benefits to more than one athlete at a given time. As such, in one configuration, a plurality of smart chairs 10 may be adjacently coupled to form a smart bench that includes a plurality of inner seating surfaces 42, each adapted to ergonomically receive and support a different user/athlete. In one configuration, the smart bench may be a single, unitary product that includes a plurality of adjacent seating surfaces 42. In another configuration, adjacent individual chairs 10 may be locally affixed to form a larger structure.

If used in connection with the sport of basketball, a smart bench may be adapted to receive and support, for example, up to five users/athletes or more at any particular time. The five users may include players currently checked into the game (e.g., during a timeout or break between quarters), players recovering after being substituted out of the game, and/or players awaiting imminent substitution into the game. In other examples, a smart bench for basketball may be adapted to receive and support up to two or three users/athletes (i.e., given that most teams play with a seven or eight man rotation, the two or three players waiting to enter/re-enter the game may be maintained in a warmed-up state).

While the present disclosure is primarily illustrated in connection with the sport of basketball, the present technology is equally applicable and useful with other sports, such as, but not limited to, American football, soccer, tennis, lacrosse, rugby, baseball, softball, hockey, gymnastics, stock car racing, open wheel racing, skiing, snowboarding, sprinting or other track and field events, swimming, field hockey, wrestling, mixed martial arts, boxing, cricket, or any events that involve intermittent periods of play and rest, events that are performed seated, or events that involve in-game player substitutions. Likewise, while the present chair has primary applicability with the athlete, one or more of the described smart chair aspects may be similarly applicable to spectators of any of the above-identified sports.

As used above, the "processor 24" is intended to include and may be embodied as one or more distinct data processing devices, each having one or more microcontrollers or central processing units (CPU), read only memory (ROM), random access memory (RAM), electrically-erasable programmable read only memory (EEPROM), a high-speed clock, input/output (I/O) circuitry, and/or any other circuitry that may be required to perform the functions described herein. The processor 24 may be local to the chair 10 and/or may include one or more remote processors or servers. In some embodiments, the "processor 24" may include and/or be in communication with one or more internet-based/cloud-based services that may provide or receive real-time data to/from the chair 10 and/or may control one or more performance or visual aspects of the chair 10.

Figure 13:
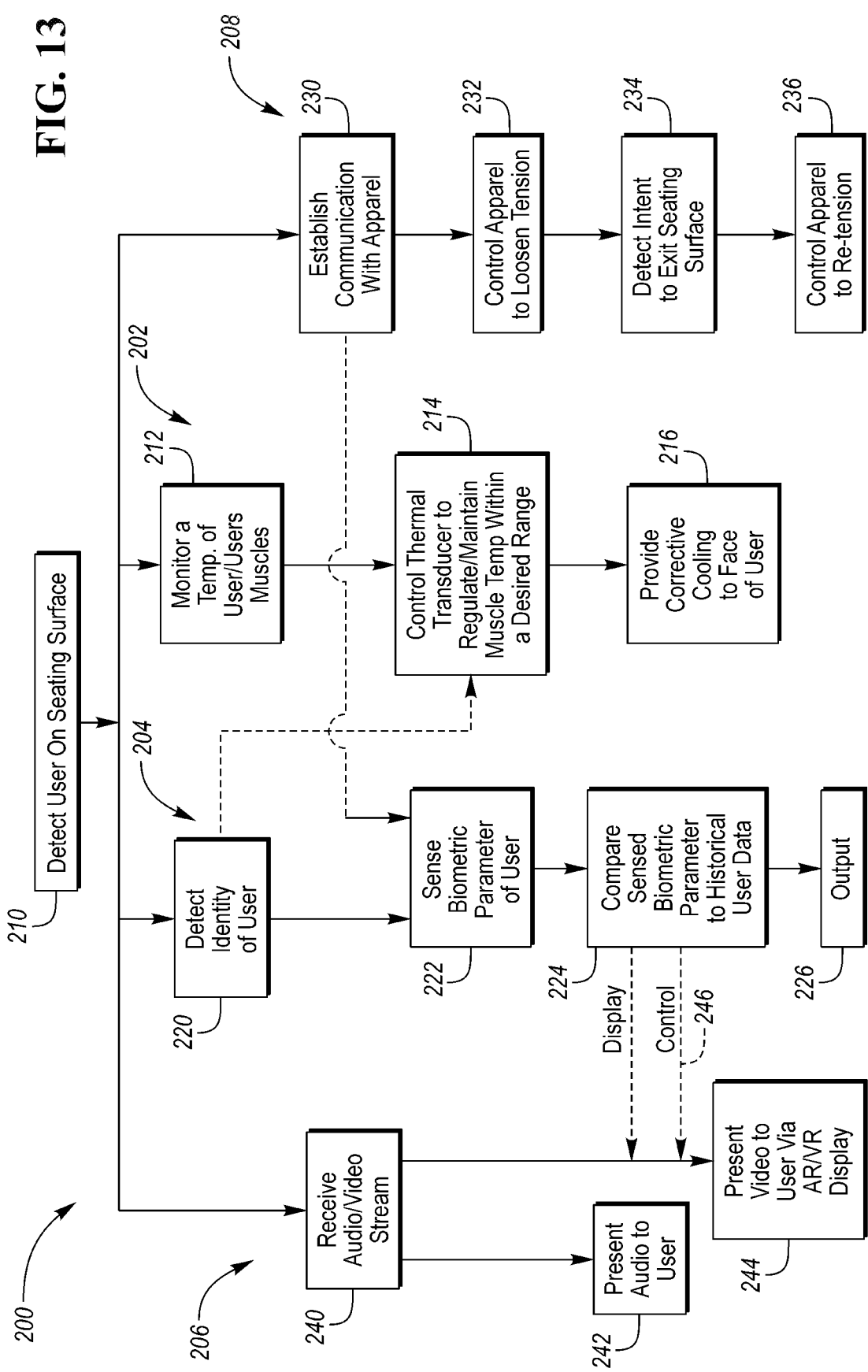
FIG. 13 is a schematic diagram illustrating functionality that may be performed by a processor of a smart chair.

FIG. 13 schematically illustrates an embodiment of a method 200 of operation of the chair 10 from the perspective of the processor 24. The method 200 generally begins at 210 with the detection of the presence of a user/athlete. As noted above, presence may be detected by monitoring, for example, one or more load cells, strain gauges, capacitive sensors, thermal sensors, or RF sensors for the presence of a user on the seating surface 42.

Once a user is detected at 210, using the connected hardware, the processor 24 may perform one or more thermal management functions (generally at 202), one or more biometric sensing functions (generally at 204), one or more display or communication functions (generally at 206), and/or one or more apparel/footwear integration functions (generally at 208).

As described above, to provide the thermal management functionality 202 the processor 24 may begin by monitoring a temperature of a user and/or the user's muscles (at 212). This monitoring may be accomplished by, for example, by polling one or more thermal sensors distributed across the seating surface 42. Once the temperature of the user (or the user's thermal profile across their major muscle groups) is understood, the processor 24 may operate one or more thermal transducers to regulate and/or maintain a muscle temperature (or a thermal profile) at a desired set point or within a desired temperature range (at 214). This heating/cooling is preferably accomplished via direct conduction between the thermal transducer and the user 36. More specifically, the heating/cooling may involve actively supplying thermal energy to the user, such as via a Peltier heating element or resistive heating element, and/or it may involve actively sinking thermal energy from the user, such as via a Peltier cooling element, or other fluid based refrigeration techniques.

In one embodiment, the target temperature(s) may received directly from the user. For example, the user may specify a target temperature in degrees, or via a qualitative 1-10 value. In an embodiment, the processor 24 may apply a hysteresis to this set point to establish a controlled temperature range. In another embodiment, the target temperature(s) may be received from an associated database, for example, based on the identity of the user (which may be detected at 220 via the identity sensing capabilities described in FIG. 6). The user's ideal target temperature or thermal profile may be a predetermined temperature/profile that accounts for the nature of the sporting activity, the user's physiological makeup and conditioning, and the user's thermal preferences. To further provide a feeling of relief or cooling following a period of exertion (i.e., where the temperatures monitored at 212 are at or above the desired set point), the processor 24 may direct convective cooling at the user's face, head, and neck (at 216).

The biometric functions (generally at 204) may operate using or on the basis of the health sensing capabilities 52 described above. More specifically, following the identification of the user at 220, the processor 24 may monitor one or more biometric sensors, load cells, or other health sensing capabilities 52 (at 222) to understand the real-time condition of the user. These sensed parameters may be compared to historical user data (at 224) to assess the user's real-time condition as a function of a normal or peak condition. The processor 24 may further correlate user condition levels with historical performance data so that the real-time condition may be indicative of athletic readiness (i.e., where a greater degree of exhaustion may result in a decreased athletic ability). Such an analysis may be performed, for example, via a multiple regression model. These health statistics may then be output (at 226) to coaching staff and/or media, such as shown in FIG. 6, to permit improved player substitution strategies and/or a deeper understanding of the state of the player/team. In one configuration, the processor 24 may determine a composite health index that represents a level of exhaustion, a ratio of current condition to peak condition, or a ratio of a current health-modeled performance level with an optimal health-modeled performance level.

In one embodiment, the health/biometric sensing capabilities may be integrated into the user's apparel and may log data throughout the competition. In that case, the processor 24 may establish communication with the apparel at 230, at which time the processor 24 may then retrieve the biometric data (at 222) directly from the wearable sensor.

As further discussed above, in the case of auto-tensioning footwear/apparel (collectively "apparel"), once communication is established with the apparel (at 230), the processor 24 may instruct the apparel to loosen and/or release any applied compression (at 232). Such a capability may allow the user to more completely relax during a period of rest. This capability may involve instructing the apparel to relieve tension applied through/across a shoe upper, a compression sleeve, leggings, knee, ankle, or wrist braces, and/or headgear.

Following the loosening of the apparel at 232, if the processor 24 detects that a user is intent on standing up and/or exiting the seating surface (at 234), it may communicate with the apparel to instruct re-tensioning (at 236). In some embodiments, however, the re-tensioning may instead occur simply via a break in communication between the apparel and the processor 24 (i.e., rather than an overt instruction). In such an embodiment, the default state of the apparel may be "tensioned," while the processor 24 simply "holds" the apparel in a looser configuration while the user is seated.

As further illustrated in FIG. 13, the processor 24 may also coordinate various display/communication functions at 206. As shown, the processor 24 may receive (and/or outwardly transmit) one or more audio and/or video streams at 240. Audio streams, such as advice from a coach, or communications between athletes may be presented to the user via a speaker/microphone (at 242), and visual streams may be presented to the user via a connected display system 18 (at 244). In some embodiments, such as the e-sporting case described above, biometric sensing may be capable of controlling aspects of the video stream (at 246), such as by narrowing a field of view or focus of the video stream.

In some embodiments, the video stream output via the display system 18 (at 244) may include, for example, play diagrams, advanced statistics on the opposing team's in-game tendencies, probabilistic heat maps representing opponent positioning, tendencies, or areas of the field that represent the highest likelihood of success, and/or real-time player health or fitness summaries.

Displayed play diagrams may either incorporate real-time tracking of the opposing team, such as may be acquired using cameras with image recognition capabilities, to analyze routes or responses to a given action on the field. Additionally, they may present one or more plays selected by a coach or via predictive computational techniques (i.e., a play that maximizes a probability of a successful outcome as defined by the coaching staff or by a recognition of the context of the situation). If being used as a forward looking strategy, such as during a timeout or stoppage in play, the play diagram may animate in time to better illustrate the pace or sequence of the drawn-up play.

Displayed advanced statistics may include, for example, team formation probabilities, team route/play probabilities, player directional tendencies, player/team shot selection tendencies, player/team shooting percentages by location, batting tendencies, or the like. Such tendencies may be recognized using player tracking capabilities (e.g., optical or RF), and may be processed using advanced computational techniques such as cluster analysis, pattern matching, neural networks, support vector machines, probabilistic methods, or other such techniques. Probabilistic heat maps may then be an effective manner to visualize these computed statistics. As may be appreciated, the heat map may dynamically color a portion of the playing area (whether using AR or via a top view that is overlaid across a portion of the user's field of view).

Finally, real-time player health or fitness summaries may provide readouts of different biometric parameters, how those parameters compare to a user's historical trends, and/or how the user has previously performed when under a similar physical condition/level of exhaustion. Using these trends, the processor 24 may compute a composite health indicator that illustrates how far the user is away from his/her optimal physiological condition (i.e., the condition that has historically provided optimal performance).

While the above-referenced information may be displayed to the user via the display system 18, it may also be also be presented to one or more spectators via the media production device 32 and/or the A/V facilities 34. In some embodiments, the display to one or more spectators may be in the form of an AR display (i.e. for users that are present live at the sporting venue), in the form of a VR display (i.e., for users that are not live at the venue), or in the form of infographics that may be displayed through a television or streaming video broadcast.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment. The terms "comprises," "comprising," "including," and "having," are inclusive and therefore specify the presence of stated items, but do not preclude the presence of other items. As used in this specification, the term "or" includes any and all combinations of one or more of the listed items. When the terms first, second, third, etc. are used to differentiate various items from each other, these designations are merely for convenience and do not limit the items.

The invention claimed is:

1. A sport chair comprising:
a seating surface operative to support a user;
a processor configured to:
detect the presence of a user on the seating surface;
establish communication with an article of apparel on the body of the user;
receive an indication of a physiological parameter of the user from a biometric sensor provided with the article of apparel; and
output the physiological parameter to a display.

2. The sport chair of claim 1, wherein the physiological parameter includes a magnitude of an impact force experienced by the user prior to the user being present on the seating surface.

3. The sport chair of claim 2, wherein the physiological parameter includes an indication of a location where the impact force was experienced on the user.

4. The sport chair of claim 1, further comprising the display, and wherein the display is integral to the chair.

5. The sport chair of claim 4, wherein the display includes a portion that is transparent such that the user can see through the display.

6. The sport chair of claim 1, further comprising an inductive charging transmitter; and
wherein the processor is operative to charge a battery associated with the article of apparel on the body of the user by transmitting a magnetic field via the inductive charging transmitter.

7. The sport chair of claim 1, wherein the physiological parameter includes at least one of hydration, weight, heart rate, respiration rate, or galvanic skin response.

8. The sport chair of claim 1, wherein the processor is further configured to control the article of apparel to alter a tension applied throughout the article of apparel.

9. The sport chair of claim 8, wherein the processor is further configured to receive a tension feedback signal from the article of apparel indicative of an amount of pressure exerted by the article of apparel against the user; and
wherein the processor is operative to use the tension feedback signal to control the tension applied throughout the article of apparel.

10. The sport chair of claim 1, wherein the processor is further configured to:
determine an identity of the user; and
store the sensed physiological parameter to a database in connection with the identity of the user.

11. The sport chair of claim 10, wherein the processor is further configured to:
retrieve historical physiological parameters for the user from the database; and
output a comparison of the sensed physiological parameter to the historical physiological parameters via the display.

12. A method comprising:
detecting the presence of a user on a seating surface of a chair;
establishing communication between a processor associated with the chair and an article of apparel on the body of the user;
receiving, via the processor, an indication of a physiological parameter of the user from the article of apparel, the physiological parameter being sensed by a biometric sensor provided with the article of apparel; and
outputting the physiological parameter to a display.

13. The method of claim 12, wherein the physiological parameter includes a magnitude of an impact force experienced by the user prior to the user being present on the seating surface; and
wherein outputting the physiological parameter to the display includes outputting the magnitude of the impact force to the display.

14. The method of claim 13, wherein the physiological parameter includes an indication of a location where the impact force was experienced on the user; and
wherein outputting the physiological parameter to the display further includes outputting the location to the display.

15. The method of claim 12, further comprising inductively charging a battery associated with the article of apparel on the body of the user by transmitting a magnetic field from an inductive charging transmitter on the chair.

16. The method of claim 12, further comprising controlling the article of apparel, via the processor, to alter a tension applied throughout the article of apparel.

17. The method of claim 16, further comprising receiving a tension feedback signal from the article of apparel, the tension feedback signal indicative of an amount of pressure exerted by the article of apparel against the user; and
wherein controlling the article of apparel to alter a tension applied throughout the article of apparel is in response to the received tension feedback signal.

18. The method of claim 12, further comprising:
determining an identity of the user, via the processor; and
storing the sensed physiological parameter to a database in connection with the identity of the user.

19. The method of claim 18, further comprising:
retrieving historical physiological parameters for the user from the database; and
outputting a comparison of the sensed physiological parameter to the historical physiological parameters via the display.

20. A method comprising:
detecting the presence of a user on the seating surface of a chair;
establishing communication between a processor associated with the chair and an article of apparel on the body of the user; and
controlling the article of apparel, via the processor, to reduce a tension applied throughout the article of apparel.

\* \* \* \* \*